(12) United States Patent
Schaz et al.

(10) Patent No.: US 11,324,517 B2
(45) Date of Patent: May 10, 2022

(54) SAW BLADE

(71) Applicant: AESCULAP AG, Tuttlingen (DE)

(72) Inventors: Uwe Schaz, Neuhausen (DE); Uwe Mattes, Tuttlingen (DE); Markus Schäfer, Bad Dürrheim (DE); Elke Moser, Denkingen (DE)

(73) Assignee: AESCULAP AG, Tuttlingen (DE)

( * ) Notice: Subject to any disclaimer, the term of this patent is extended or adjusted under 35 U.S.C. 154(b) by 294 days.

(21) Appl. No.: 16/618,889

(22) PCT Filed: Jun. 11, 2018

(86) PCT No.: PCT/EP2018/065326
§ 371 (c)(1),
(2) Date: Dec. 3, 2019

(87) PCT Pub. No.: WO2018/228979
PCT Pub. Date: Dec. 20, 2018

(65) Prior Publication Data
US 2020/0163680 A1 May 28, 2020

(30) Foreign Application Priority Data

Jun. 12, 2017 (DE) .......................... 102017112872.7

(51) Int. Cl.
*A61B 17/14* (2006.01)
*B23D 61/00* (2006.01)
(52) U.S. Cl.
CPC .......... *A61B 17/142* (2016.11); *B23D 61/006* (2013.01)
(58) Field of Classification Search
CPC ..... A61B 17/14; A61B 17/142; A61B 17/144; B23D 61/006
See application file for complete search history.

(56) References Cited

U.S. PATENT DOCUMENTS

| 7,837,690 | B2 * | 11/2010 | Metzger | A61B 17/157 |
| | | | | 606/87 |
| 8,870,883 | B2 * | 10/2014 | Metzger | A61B 17/155 |
| | | | | 606/88 |
| 9,027,452 | B2 * | 5/2015 | Nagy | B23D 61/006 |
| | | | | 83/835 |
| 9,522,007 | B2 * | 12/2016 | Servidio | A61B 17/142 |
| 2004/0138670 | A1 * | 7/2004 | Metzger | A61B 17/157 |
| | | | | 606/88 |
| 2006/0009796 | A1 * | 1/2006 | Carusillo | A61B 17/14 |
| | | | | 606/178 |
| 2006/0123959 | A1 * | 6/2006 | Bocast | B23D 61/006 |
| | | | | 83/13 |

(Continued)

FOREIGN PATENT DOCUMENTS

| CN | 201414821 Y | 3/2010 |
| CN | 102670274 A | 9/2012 |

(Continued)

OTHER PUBLICATIONS

First Chinese Office Action, Application No. 201880039220.1, dated Apr. 17, 2020, 17 pages.

(Continued)

*Primary Examiner* — Eric S Gibson
(74) *Attorney, Agent, or Firm* — Culhane Meadows PLLC; Christopher A. Rothe

(57) ABSTRACT

A saw blade of a bone saw machine includes a distally arranged or configured row of saw teeth and a proximally arranged or configured coupling region for coupling the saw blade with an oscillating rotating tool receptacle of the bone saw machine. The saw blade is designed with two counter-rotating curvatures or bends approximately in the manner of an S shape.

12 Claims, 3 Drawing Sheets

(56) References Cited

U.S. PATENT DOCUMENTS

| | | | | |
|---|---|---|---|---|
| 2014/0012265 A1* | 1/2014 | Servidio | ............... | A61B 17/14 606/82 |
| 2014/0230626 A1* | 8/2014 | Puzio | .................. | B23D 61/006 83/697 |
| 2015/0039037 A1* | 2/2015 | Donner | ............. | A61B 17/1739 606/279 |
| 2019/0231364 A1 | 8/2019 | Walen et al. | | |
| 2020/0163680 A1* | 5/2020 | Schaz | ................. | A61B 17/142 |

FOREIGN PATENT DOCUMENTS

| | | |
|---|---|---|
| CN | 206183324 U | 5/2017 |
| DE | 202013004984 U1 | 5/2014 |
| DE | 202013005232 U1 | 5/2014 |
| DE | 102016103903 A1 | 9/2017 |
| EP | 2974677 A1 | 1/2016 |
| JP | 2006055306 A | 3/2006 |

OTHER PUBLICATIONS

German Search Report for German Application No. 10 2017 112 872.7, with English translation, dated Dec. 22, 2017, 10 pages.
International Search Report and Written Opinion for International Application PCT/EP2018/065326, dated Sep. 19, 2018, 8 pages.
Japanese Notice received in Japanese Patent Application No. 2019-572843, 2 pages. (with translation).
Japanese Office Action received in Japanese Patent Application No. 2019-572843, 16 pages. (with translation).

* cited by examiner

SAW BLADE

CROSS-REFERENCE TO RELATED APPLICATIONS

This application is the United States national phase entry of International Application No. PCT/EP2018/065326, filed Jun. 11, 2018, which claims the benefit of priority of German Application No. 10 2017 112 872.7, filed Jun. 12, 2017. The contents of International Application No. PCT/EP2018/065326 and German Application No. 10 2017 112 872.7 are incorporated by reference herein in their entireties.

FIELD

The present invention relates to an exchangeable surgical saw blade for an oscillating medical/surgical saw machine.

BACKGROUND

In up-to-date surgery, for severing bones such as the hip joint, the sternum, etc. electric bone saw machines are used as they are developed and manufactured inter alia also by the applicant of the present invention. A bone saw machine of this type comprises a housing which is simultaneously also in the form of a handhold and in which a drive unit for driving a vibrating head in an oscillating manner is accommodated. The vibrating head includes a tool receptacle in which a saw blade is inserted in a detachable and thus exchangeable manner.

The saw blade takes approximately the shape of a tongue with a row of saw teeth at the front edge thereof distal to the vibrating head in such a way that, in the case of an oscillating rotational movement of the vibrating head, the row of saw teeth is moved to oscillate on an orbit and in this way applies a sawing effect to a bone, for example.

From prior art a saw blade of the afore-defined species is known, as it is distributed, inter alia, by the applicant of the present invention. Said saw blade in a top view takes a substantially rectangular shape with a coupling region preferably configured as a punching on an end portion located in the longitudinal direction of the rectangular shape and a row of saw teeth on the other front edge of the saw blade, when viewed in the longitudinal direction of the rectangular shape. The preferred punching results in a kind of resiliently pivotable locking tongue which can be detachably engaged with an appropriately configured locking/click mechanism which is formed on a tool receptacle of a generally known bone saw machine.

For better comprehension, in FIG. 5 a bone saw machine of this type is shown.

Consequently, the known bone saw machine has a sleeve-shaped or pistol-type housing, preferably made from plastic, aluminum material, titanium material or stainless steel, in which housing a drive not shown in more detail such as an electric motor including the pertinent control electronics is accommodated. At the distal end of the housing a vibrating head is disposed at/in which the tool receptacle and, resp., a plug-in coupling is rotatably supported. Via a gear mechanism the drive motion of the electric drive/motor is transmitted to the tool receptacle and, resp., plug-in coupling such that the latter performs an oscillating rotational movement of a predetermined frequency.

The tool receptacle preferably forms a kind of dovetail guide including the integrated click/locking mechanism between the two opposite clamping rails of the dovetail guide. When, thus, the afore-described saw blade is introduced or inserted into the dovetail guide in the longitudinal direction thereof (between the clamping rails of the dovetail guide), the locking tongue finally engages with the click/locking mechanism and thus locks the saw blade to the tool receptacle.

When taking the bone saw machine into operation, the tool receptacle is set in an oscillating rotational movement which is transmitted to the saw blade. In this way, the row of saw teeth is made to reciprocate on an orbit whose radius corresponds to the distance between the axis of rotation of the tool receptacle and the distal free front edge of the saw blade.

In order to facilitate handling of the bone saw machine of such structure, the distal free front edge of the saw blade is formed to be curved corresponding to the afore-defined orbit rather than to be linear. This helps prevent the respective last teeth of the row of saw teeth from getting caught in the bone material, which might result in a non-controllable vibrating motion of the bone saw machine.

It has turned out, however, that the foregoing shaping of the saw blade constitutes a drawback in so far as it is difficult to longitudinally guide said saw blade beneath a patient's skin for example when sawing a sternum. Even in the case that the straight saw blade is aligned at an angle with the machine housing, for example of about 45°, by appropriately rotating the tool receptacle in the construction position, the saw blade cannot be driven satisfactorily forward beneath the patient's skin in the sawing direction without hurting the patient's skin. In addition, the bone saw machine must enable appropriate adjustments which would render the machine more expensive.

Ultimately, it was found that, irrespective of the angular position of the saw blade relative to the patient's skin, injuries of soft tissue still might occur, especially when the last saw tooth of the row of saw teeth contacts and then cuts soft tissue during an uncontrolled swivel movement of the machine.

SUMMARY

In view of the afore-stated problems, it is the object of the present invention to provide a saw blade for (or of) a bone saw machine which enables improved handling when sawing a sternum beneath the patient's skin, for example. It is a preferred objective to largely minimize the risk of inadvertent injury of the patient's soft tissue.

Basically, a saw blade for or, resp., of a bone saw machine includes a proximally arranged or configured coupling region which defines a coupling or inserting direction and which is provided and configured for coupling or inserting the saw blade with/in a tool receptacle of the bone saw machine rotating about an axis of rotation in an oscillating manner. Moreover, the saw blade includes a row of saw teeth arranged or configured on a distal front edge of the saw blade such that the central axis thereof aligned perpendicularly to the row of saw teeth substantially intersects the coupling region of the saw blade and preferably the axis of rotation, when the saw blade is coupled to or inserted in the tool receptacle. In this way, the row of saw teeth moves substantially tangentially along an orbit, when the tool receptacle is rotated in an oscillating manner. It is a core of the present invention that, according to the foregoing definitions, the central axis (M) and the coupling or inserting direction stand and are aligned or alignable, resp., relative to each other at an angle unequal to 0° and, resp., 180°, preferably at approx. 45°.

In this way, it is possible to insert the saw blade even into those tool receptacles whose defined inserting direction deviates from the afore-defined central axis.

In a concrete preferred embodiment, the saw blade is configured with two (counter-rotating) curvatures approximately in S shape rather than linearly. In this manner, it is especially easily possible to tilt the sawing direction of the saw blade via the one free leg of said substantial S shape (at which the row of saw teeth is formed/configured) optionally relative to the inserting direction of the tool receptacle (inserting coupling) and, at the same time, to utilize the angular positions/inserting directions of the tool receptacle (inserting coupling) predetermined by a bone saw machine (without having to vary them with great effort) by appropriately inclining the other free leg (at which the coupling region, preferably the locking tongue, is formed/arranged).

An intermediate web connecting the two free legs of the quasi S shape may optionally be easily dimensioned so that a linear extension of the central axis of the row of saw teeth, which in this case also constitutes the central axis of the one free/distal leg (at which the row of saw teeth is formed/arranged), intersects the coupling region of the saw blade, preferably the axis of rotation of the tool receptacle so that the row of saw teeth reciprocates tangentially along the selected orbit. In this context, it is further pointed out that the tem' "sawing direction" is understood to be the direction which extends perpendicularly to the row of saw teeth and thus corresponds to the central axis of the row of saw teeth and, resp., of the one free/distal leg of the S shape.

Alternatively to the foregoing concrete embodiment, it would also be imaginable to provide merely one (single) curvature which separates the proximal leg forming the coupling region from the distal leg forming/supporting the row of saw teeth, wherein in this case (merely) the row of saw teeth is aligned/inclined relative to the central axis of the distal leg such that the central axis of the row of saw teeth extends at an angle unequal to 0° or 180° with the central axis of the distal leg. This allows to achieve that the central axis of the row of saw teeth again approximately intersects the coupling region and preferably the axis of rotation of the tool receptacle.

In other words, the saw blade according to the invention for severing bones in accordance with a first aspect of the present invention includes a coupling region for inserting (and locking) into the tool receptacle and, resp., into the inserting coupling of the bone saw machine. The coupling region defines, by its configuration, a predetermined inserting direction along which the saw blade can be inserted into the tool receptacle of the bone saw machine. For example, the tool receptacle for this purpose has a type of dovetail guide or two opposite clamping rails/clamping jaws between which the saw blade is inserted so as to be capable of transmitting torques to the saw blade. Further, between the clamping jaws a detent lug or a recess can be formed preferably in the area (on) of the axis of rotation of the tool receptacle which locks with an appropriately shaped locking element/locking section at the saw blade in the completely inserted condition and thus prevents the saw blade from being inadvertently removed from the tool receptacle.

Finally, the axis of rotation (predetermined by the saw) which is located within the coupling region is fixed such that, with an oscillating movement of rotation of the tool receptacle/inserting coupling about the axis of rotation thereof, the inserted saw blade performs an oscillating movement of rotation together with the tool receptacle/ inserting coupling in which the row of saw teeth moves substantially tangentially along or on an orbit. The row of saw teeth (also referred to as saw toothing) which consequently extends at least substantially along a tangential direction relating to the axis of rotation of the tool receptacle/inserting coupling, is aligned so that the defined saw feeding direction and, resp., central axis of the tooth row thereof (substantially perpendicularly to the saw toothing direction) is rotated at/twisted with an angle unequal to 180° (or 0°) with the inserting direction, preferably within a range from 15° to 80°, especially from 30° to 60° and further preferred by 45° (tolerance of +/−5°).

Another core of the invention provides to have the row of saw teeth (saw toothing) not to extend over the entire distal free front edge of the saw blade according to the invention but to insert it between two non-toothed end portions of the distal free front edge, wherein the two non-toothed end portions of the distal free front edge merge into the lateral edges of the saw blade each forming a forwardly/laterally convex rounding. Thus, the front-side saw toothing and especially the last teeth thereof are largely prevented from engaging in the soft tissue even when the machine is (inadvertently) swiveled.

BRIEF DESCRIPTION OF THE DRAWING FIGURES

Hereinafter the invention will be illustrated in detail by way of a preferred example embodiment with reference to the accompanying figures.

DETAILED DESCRIPTION

Figure 1:
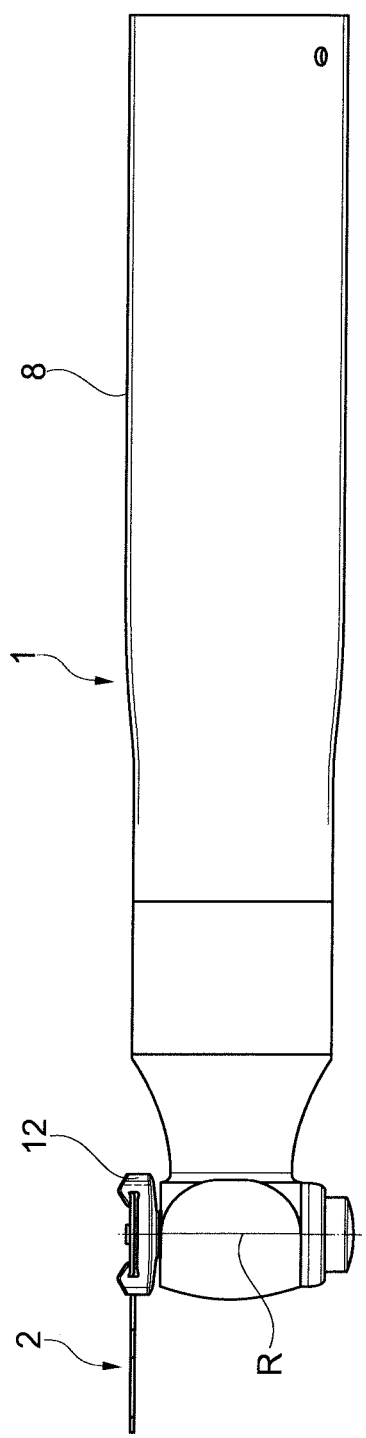
FIG. 1 shows the top view of a bone saw machine with an attached saw blade according to a preferred example embodiment of the present invention.
Figure 2:
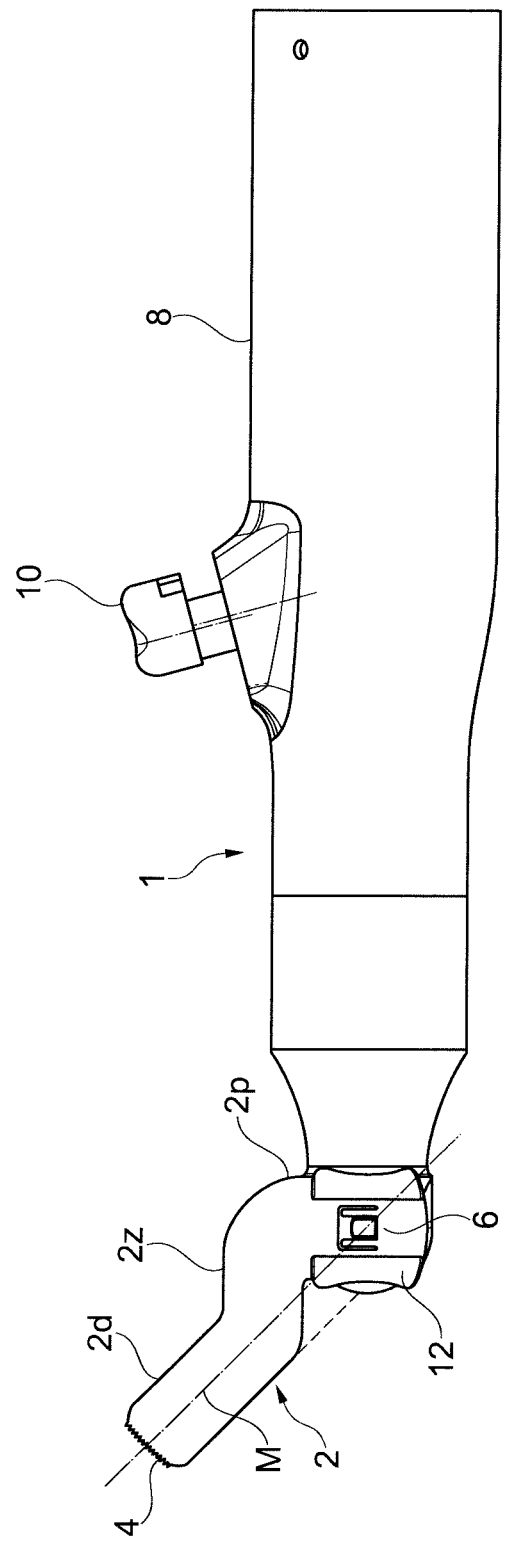
FIG. 2 shows the side view of the bone saw machine of FIG. 1 with the attached saw blade according to the preferred example embodiment of the present invention.

FIGS. 1 and 2 illustrate a bone saw machine 1 with a preferably exchangeable saw blade 2 according to a preferred example embodiment of the present invention which saw blade 2 is configured, in contrast to a known saw blade, with two (counter-rotating) curvatures or bends approximately in the manner of an S shape rather than linearly.

The saw blade 2 according to the invention thus has a first distal leg 2d and a second proximal leg 2p which are aligned at an angle unequal to 0° or unequal to 180° (presently approx. 45°) relative to each other. The two legs 2d, 2p of the saw blade 2 which is wound quasi in S shape are interconnected (formed in one material piece) via an intermediate web 2z.

The first distal leg 2d is preferably linearly configured and includes a first distal front edge which is formed or provided with a saw toothing/row of saw teeth 4 of preferably less than/equal to 20 mm of tooth row length (measured between the respective outermost teeth) extending approximately at right angles/perpendicularly/rectangularly with a central axis M of the first distal leg 2d. The second proximal leg 2p is equally configured to be preferably linear and in its distal end portion includes a coupling region 6 as it is known already from the prior art according to the foregoing description. Therefore, in this context the foregoing description passages can be referred to. This coupling region 6 thus is provided and configured to (lock)/engage with the (generally known) tool receptacle/inserting coupling of a bone saw machine.

Such bone saw machine 1 is symbolized in FIGS. 1 and 2 and in the present case includes a sleeve-shaped housing 8 which also serves as handle piece and which is equipped with operating handles such as push button switches 10 or the like. The motor (not shown) accommodated therein drives the tool receptacle/inserting coupling 12, as described before by way of prior art, for the oscillating movement of rotation thereof about an axis of rotation R which oscillation movement is transmitted to the saw blade 2 tightly locked with the tool receptacle 12. The row of saw teeth 4 performs a reciprocating movement along an orbit K whose center forms the axis of rotation R of the tool receptacle.

Figure 3:
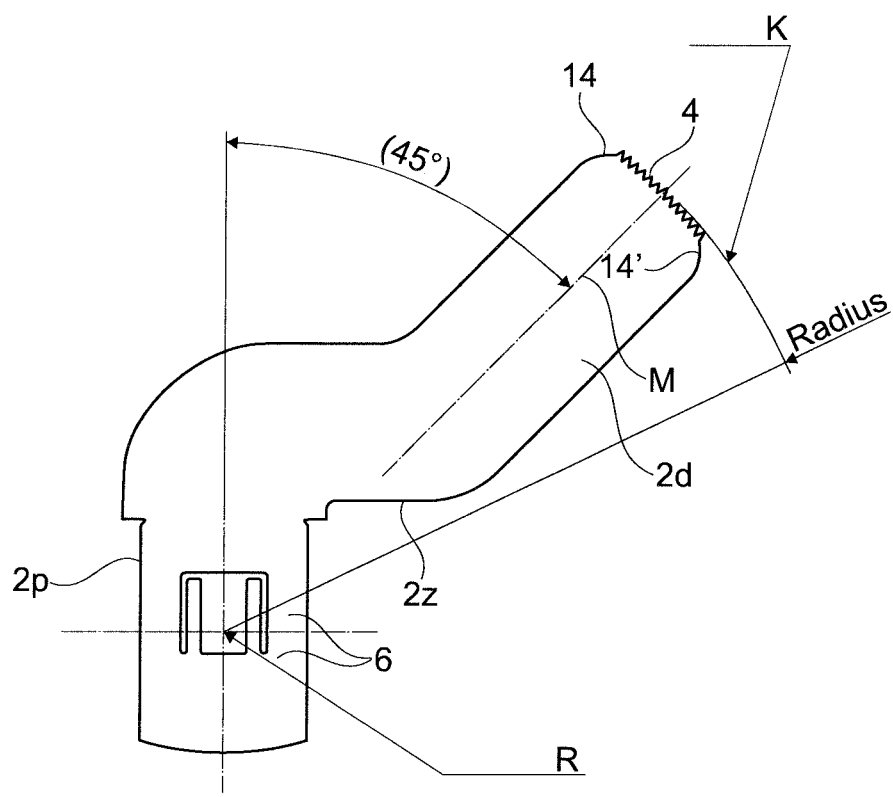
FIG. 3 shows the right-hand top view of the saw blade according to the preferred example embodiment of the present invention.
Figure 4:
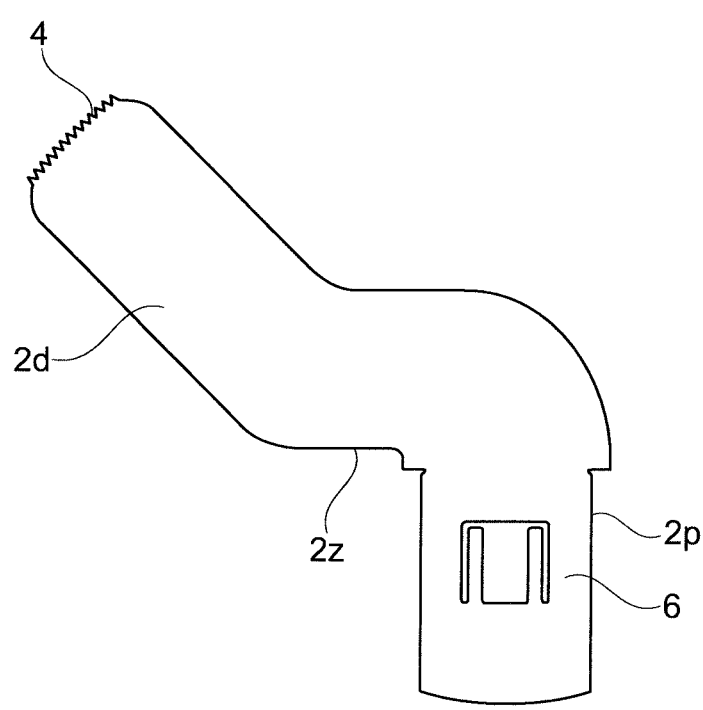
FIG. 4 shows the left-hand top view of the saw blade according to the preferred example embodiment of the present invention.

So that the row of saw teeth 4 is aligned substantially tangentially with the orbit K despite the quasi S shape of the saw blade 2, the afore-described intermediate web 2z according to FIGS. 3 and 4 is configured so that it extends preferably at right angles with the second proximal leg 2p and has/will have a length that is selected so that a central axis M of the first distal leg 2d (in the imaginary extension thereof) intersects the axis of rotation R of the tool receptacle 12 and, resp., of the inserting coupling, when the saw blade is correctly inserted in the tool receptacle. In the present example, the pivot point of the saw blade is located in the coupling region thereof, preferably of the locking tongue formed in the proximal leg 2p.

The row of saw teeth 4 is curved rather than linear, the radius of curvature thereof corresponding substantially to that of the orbit K along which it reciprocates. Moreover, the row of saw teeth 4 according to FIGS. 3 and 4 is shorter than the length of the distal front edge of the saw blade 1 so that a non-toothed remaining portion 14, 14' of the distal front edge connects to/remains at each of the two ends of the row of saw teeth 4. Said two remaining portions 14, 14' are convexly rounded in the distal direction and in the lateral direction and in this way merge into the respective lateral edges of the saw blade 1 in curved shape. In this context, it is pointed out that all edge transitions between the two legs and the intermediate piece are equally rounded to minimize any risk of injury.

Figure 5:
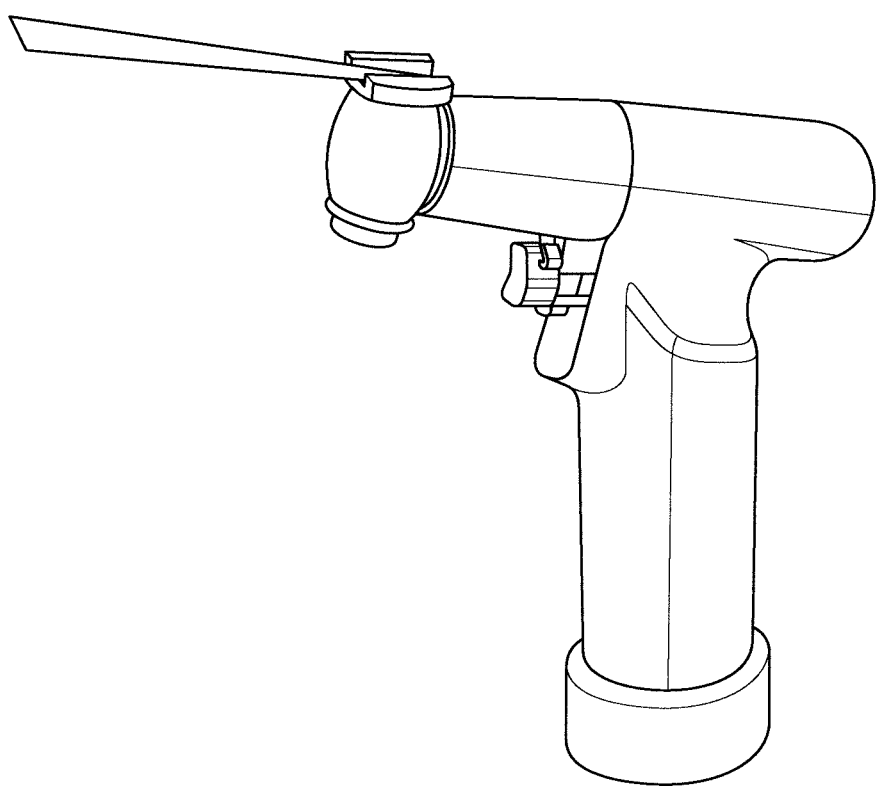
FIG. 5 shows the side view of a bone saw machine with an attached saw blade as known from prior art.

It is finally to be mentioned that the bone saw machine shown in FIGS. 1 and 2 is only exemplary and can be replaced with a bone saw machine according to FIG. 5. Also, the coupling between the saw blade and the tool receptacle shown and described in the beginning is found in a lot of saw cutting machines (and thus is generally known prior art), to be sure. However, it has merely the function of coupling the saw blade to the tool receptacle in a possibly exchangeable manner and can be replaced with a different coupling design without the core of the present invention being affected. I.e. irrespective of how the saw blade is coupled to the tool receptacle, it is basically possible to align the proximal leg individually with the respective coupling by the quasi S shape of the saw blade and to maintain the distal leg at the shown direction of inclination relative to the tool receptacle and, resp., the longitudinal machine axis, for example, wherein the length of the intermediate piece can be individually adjusted so that the central axis of the distal leg intersects the axis of rotation of the tool receptacle in the area of the coupling.

Summing up, the present invention relates to a preferably exchangeable saw blade of a bone saw machine including a distally arranged or configured row of saw teeth and a proximally arranged or configured coupling region for coupling the saw blade with an oscillating rotating tool receptacle of the bone saw machine, wherein the saw blade is designed with two counter-rotating curvatures or bends approximately in the manner of an S shape.

The invention claimed is:

1. A saw blade for a bone saw machine comprising: a coupling region defining a coupling or inserting direction for coupling or inserting the saw blade with/into a tool receptacle of the bone saw machine rotating about an axis of rotation in an oscillating manner, and comprising a row of saw teeth arranged or configured at a distal front edge of the saw blade in such way that a central axis thereof aligned perpendicularly to the row of saw teeth substantially intersects the coupling region, when the saw blade is coupled to or inserted in the tool receptacle, wherein the central axis and the coupling or inserting direction are at an angle between 0° and 180° relative to each other, the saw blade being designed with two counter-rotating curvatures or bends approximately in an S shape, the saw blade including, by virtue of the two counter-rotating curvatures or bends, a first distal leg and a second proximal leg that are aligned at an angle between 0° and 180° relative to each other, the first distal leg and second proximal leg of the saw blade being interconnected via an intermediate web, and the first distal leg being configured to be linear and having a distal front edge configured or provided with the row of saw teeth, the central axis of the row of saw teeth being the central axis of the first distal leg, and the second proximal leg being equally configured to be linear and including or forming the coupling region in its proximal end portion.

2. The saw blade according to claim 1, wherein the row of saw teeth is aligned substantially tangentially with an orbit along which it reciprocates with an oscillating movement of rotation of the tool receptacle in a condition of being inserted in the tool receptacle, for which purpose the intermediate web has or will have such length that the central axis of the first distal leg substantially intersects the coupling region when the saw blade is coupled with or inserted in the tool receptacle.

3. The saw blade according to claim 2, wherein the row of saw teeth is curved, wherein the radius of curvature thereof substantially corresponds to that of the orbit along which it reciprocates in a condition of being inserted in the tool receptacle, while the tool receptacle rotates in an oscillating manner.

4. The saw blade according to claim 2, wherein the intermediate web has or will have such length that the central axis of the first distal leg substantially intersects the axis of rotation of the tool receptacle when the saw blade is coupled with or inserted in the tool receptacle.

5. The saw blade according to claim 1, wherein the saw blade is a medical or surgical tool of a minimally invasive design.

6. The saw blade according to claim 1, wherein the row of saw teeth has a length of less than/equal to 20 mm.

7. The saw blade according to claim 1, wherein the row of saw teeth is shorter than a length of the distal front edge of the saw blade at which the row of saw teeth is configured or arranged so that the distal front edge comprises untoothed remaining portions at each end of the row of saw teeth.

8. The saw blade according to claim 7, wherein the untoothed remaining portions are convexly rounded in a distal direction and in a lateral direction and thus merge into respective lateral edges of the saw blade in a curved shape.

9. A surgical bone saw apparatus comprising a bone saw machine which includes a drive accommodated in a machine housing, wherein the drive is operatively connected to a tool receptacle for oscillating rotation thereof, which tool receptacle is supported on a distal end of the machine housing, and comprising a saw blade which is exchangeably coupled to or inserted in the tool receptacle such that the saw blade rotates together with the tool receptacle in an oscillating manner, wherein the saw blade comprises features according to claim 1.

10. The saw blade according to claim 1, wherein the central axis of the distal front edge of the saw blade which is aligned perpendicularly to the row of saw teeth substantially intersects the axis of rotation, when the saw blade is coupled to or inserted in the tool receptacle.

11. The saw blade according to claim 1, wherein the first distal leg and the second proximal leg of the saw blade are interconnected in one material piece.

12. A saw blade for a bone saw machine comprising: a coupling region arranged or configured proximally as well as defining a coupling or inserting direction for coupling or inserting the saw blade with/into a tool receptacle of the bone saw machine rotating about an axis of rotation in an oscillating manner, and comprising a row of saw teeth arranged or configured at a distal front edge of the saw blade in such way that a central axis thereof aligned perpendicularly to the row of saw teeth substantially intersects the coupling region, when the saw blade is coupled to or inserted in the tool receptacle, wherein the central axis and the coupling or inserting direction are at an angle between 0° and 180° relative to each other,
   the saw blade including a first distal leg and a second proximal leg that are aligned at an angle between 0° and 180° relative to each other,
   the first distal leg being configured to be linear and having a distal front edge configured or provided with the row of saw teeth, the central axis of the row of saw teeth being the central axis of the first distal leg, and the second proximal leg being equally configured to be linear and including or forming the coupling region in its proximal end portion.

* * * * *